(12) United States Patent
Aoki et al.

(10) Patent No.: US 8,529,929 B2
(45) Date of Patent: Sep. 10, 2013

(54) DRUG DELIVERY SYSTEM

(75) Inventors: Hiroki Aoki, Ube (JP); Koichi Yoshimura, Ube (JP); Hiromori Tsutsumi, Ube (JP); Chie Teruyama, Ube (JP); Masunori Matsuzaki, Ube (JP); Shunichi Kuroda, Suita (JP)

(73) Assignees: Yamaguchi University, Yamaguchi (JP); Osaka University, Osaka (JP)

( * ) Notice: Subject to any disclaimer, the term of this patent is extended or adjusted under 35 U.S.C. 154(b) by 312 days.

(21) Appl. No.: 12/746,157

(22) PCT Filed: Dec. 19, 2008

(86) PCT No.: PCT/JP2008/073884
§ 371 (c)(1),
(2), (4) Date: Jun. 3, 2010

(87) PCT Pub. No.: WO2009/082014
PCT Pub. Date: Jul. 2, 2009

(65) Prior Publication Data
US 2010/0285083 A1 Nov. 11, 2010

(30) Foreign Application Priority Data
Dec. 25, 2007 (JP) ................. 2007-331948

(51) Int. Cl.
*A61F 13/00* (2006.01)
*A61F 2/00* (2006.01)

(52) U.S. Cl.
USPC .......................................... 424/422; 424/423

(58) Field of Classification Search
None
See application file for complete search history.

(56) References Cited

U.S. PATENT DOCUMENTS

| 5,925,353 A | 7/1999 | Mosseri |
| 6,238,872 B1 | 5/2001 | Mosseri |
| 6,251,142 B1 * | 6/2001 | Bernacca et al. .......... 623/23.57 |

(Continued)

FOREIGN PATENT DOCUMENTS

| JP | 2001-521778 A | 11/2001 |
| JP | 2002-501408 A | 1/2002 |

(Continued)

OTHER PUBLICATIONS

Joohee Jung, et al., "Bio-nanocapsule conjugated with liposomes for in vivo pinpoint delivery of various materials", Journal of Controlled Release, 2008, pp. 255-264, vol. 126.

(Continued)

*Primary Examiner* — Carlos Azpuru
*Assistant Examiner* — Casey Hagopian
(74) *Attorney, Agent, or Firm* — Sughrue Mion, PLLC

(57) ABSTRACT

It is a main object of the present invention to provide a drug delivery system in which drugs can be changed or which can be recharged with drugs, which continuously delivers drugs at effective concentrations to local lesional sites in a body and allows the use of drugs for which it has thus far been difficult to achieve effective local concentrations for a variety of reasons and drugs which have been difficult to use due to adverse effects on tissues that are not sites of action. The present invention provides a drug delivery system comprising an indwelling medical device on which a biocompatible material having target molecules on its surface has been coated, and target-recognizing nanocarriers (e.g., bio-nanocapsules, liposomes, liposome preparations, and nanoparticles) in which drugs are encapsulated and which have target-recognizing molecules capable of specifically binding to the target molecules.

7 Claims, 9 Drawing Sheets

(56) References Cited

U.S. PATENT DOCUMENTS

| | | | |
|---|---|---|---|
| 6,264,596 B1 | 7/2001 | Weadock | |
| 2003/0082224 A1 | 5/2003 | Noujaim et al. | |
| 2004/0047891 A1* | 3/2004 | Glozman et al. | 424/423 |
| 2005/0287189 A1 | 12/2005 | Noujaim et al. | |
| 2007/0059746 A1 | 3/2007 | Kuroda et al. | |
| 2007/0098724 A1 | 5/2007 | Noujaim et al. | |

FOREIGN PATENT DOCUMENTS

| | | |
|---|---|---|
| JP | 2005-511502 A | 4/2005 |
| JP | 2007-106752 A | 4/2007 |
| WO | 02/067849 A2 | 9/2002 |
| WO | 2006/033679 A2 | 3/2006 |

OTHER PUBLICATIONS

Extended Search Report issued in corresponding European Patent Application No. 08863740.0 on Jan. 4, 2013.
K. Yoshimura et al., "Regression of abdominal aortic aneurysm by inhibition of c-Jun N-terminal kinase", Database Embase Online, 2005, Database Accession No. EMB-2005559668, Abstract.
"AN 2008-K12333", Database WPI, Week 200860, retrieved online at C:\EPOPROGS\SEA\..\..\..\epodata\ses\eplogf\internal.log on Dec. 19, 2012.

* cited by examiner

DRUG DELIVERY SYSTEM

TECHNICAL FIELD

The present invention relates to a rechargeable drug delivery system (RDDS: Rechargeable Drug Delivery System). Specifically, the present invention relates to a drug delivery system comprising an indwelling medical device having target molecules and nanocarriers having target-recognizing molecules and being capable of controlling drug release.

BACKGROUND ART

In order to realize effective drug treatment for a variety of diseases and, in particular, for local lesions, it is necessary to achieve sufficient drug concentrations at local sites of action. Meanwhile, if the concentration of a drug increases in non-lesional tissue, the drug does not exhibit effective action at all, while on the other hand, it exhibits undesirable adverse effects in many cases. Therefore, drug delivery systems have been developed in order to deliver a relevant drug to a specific in vivo local site at which drug effects are expected to be exhibited so as to selectively increase the drug concentration at the site.

A method known as a means of drug delivery comprises preparing liposomes containing a drug or drug-encapsulated microcapsules, and allowing them to accumulate at a local site in the body for controlled-release of the drug at the site to cause the relevant local action. For such method, injectable preparation of leuprorelin, which is an antitumor agent (Non-Patent Document 1), injectable preparation of alprostadil, which is a blood circulation-improving agent (Non-Patent Document 2), and the like have been realized in practice. However, such examples of methods comprising allowing liposome or microcapsule preparations to accumulate at a local site in a body and to cause the relevant drug action are based on the enhanced permeability and retention (EPR) effect. This is the property that a drug preparation intravascularly administered leaks into extravascular tissue due to vascular fragility observed at the relevant site. In such method, drug accumulation efficiency depends on tissue properties of the local site. Therefore, it is difficult to freely deliver a drug to an arbitrary site in a body. In order to solve such problem, it has been attempted to allow microcapsule surfaces to present molecules specifically recognizing local tissues in a body, such as sugar chain recognizing molecules and antibodies recognizing surface antigens of target cells, so as to increase site accumulation specificity of the microcapsulated drug (Patent Documents 1 and 2). However, in cases in which a sugar chain or a cellular surface antigen that is specific to a target local site in a body at which a drug is expected to act has not been discovered, it is difficult to deliver the drug specifically to the local site.

Meanwhile, for example, a drug-coated stent has been well known and realized in practice as a drug delivery system using an indwelling medical device to be placed in vivo (Patent Document 3). Coronary artery stents coated with an immunosuppressant or an antiproliferative drug for controlled drug release can effectively prevent restenosis after stent implantation. Therefore, they were actively used for a while. However, it was revealed that coronary artery occlusion is induced with high frequency due to thrombosis in implanted stents, causing acute myocardial infarction and sudden death. Nevertheless, it is practically impossible to remove such implanted stents, resulting in a serious medical issue.

In addition, in medical practice, it is often required to change drug type, point in time of drug action induction, and effective period, for different reasons. For instance, in the case of a drug having therapeutic effects upon a lesion that requires to use an indwelling medical device, it is necessary to deliver a sufficient dose of the drug to the lesion during a period of high lesional activity. If the drug dose is reduced or drug administration is discontinued during a period in which the lesional activity is decreased, alleviation, disappearance, or prevention of adverse effects can be expected. Then, if the lesional activity increases again, it again becomes necessary to deliver a sufficient dose of the drug to the lesion. In order to meet such demands, a variety of medical devices for delivering a therapeutic drug to a local site in a body have been developed. However, regarding the supply of a drug to a desired target site during a continuous period, many problems remain unsolved.

Aneurysms are developed as a result of localized weakening of arterial walls due to excessive degradation or abnormal synthesis of the extracellular matrix constituting arterial walls followed by gradual expansion, resulting in rupture and leading to death. Before rupture, no substantial symptoms are observed. Therefore, an "effective aneurysm treatment" must involve the prevention of rupture in order to improve prognosis. The following are examples of aneurysm treatment methods that have been proved with efficacy to date: a method comprising replacing an aneurysm site with by an artificial blood vessel by surgery; and a method comprising inserting a stent graft (an artificial blood vessel) inside a blood vessel so as to block the bloodstream to the aneurysm. Such a stent graft is designed to extend through an aneurysm artery portion so as to reach normal vascular sites existing in front and to the rear of an aneurysm. Such a stent graft inserted inside the aneurysm portion expands by itself, tightly adheres to normal vascular sites located in front and to the rear of the aneurysm, and cuts off the hemodynamic load on the aneurysm to cause therapeutic effects. Stent grafting is an effective treatment method as long as complete cutting off of the hemodynamic load on an aneurysm can be achieved. However, the main problem is that the probability of the occurrence of incomplete cutting off of the hemodynamic load on an aneurysm exists. When arterial wall fragility and/or aneurysm expansion worsen after stent graft treatment, tight adhesion of a stent graft to the arterial wall becomes insufficient, and this could result in incomplete cutting off of the hemodynamic load on an aneurysm (endoleak) in some cases. Once the cutting off of the hemodynamic load on an aneurysm becomes incomplete, it is impossible for a stent graft to prevent the progression of aneurysm expansion and rupture. Therefore, it is important to completely maintain the tight adhesion of a stent graft to the arterial wall by effectively inhibiting pathological changes associated with aneurysm via drug treatment. At the same time, if regression of aneurysm can be realized via drug treatment, tight adhesion of a stent graft to the arterial wall and cutting off of the hemodynamic load on the aneurysm wall are completely possible to maintain in a more secure manner, resulting in significant improvement in outcomes of stent graft treatment.

JNK (c-Jun N-terminal kinase) inhibitors are drug that have been exclusively proven to induce aneurysm regression. Therefore, aneurysm regression via drug treatment has become probably possible in practice (Non-Patent Document 3). However, when such drugs are systemically administered, undesirable adverse effects could be observed. For example, known adverse effects of doxycycline are poor appetite, nausea, vomiting, diarrhea, rash, nephrotoxicity, and anemia. The use of antibiotics such as roxithromycin and tetracycline derivatives can induce widespread presence of antibiotic-resistant pathogens (Non-Patent Document 4). Also, regarding adverse effects of systemic administration of JNK inhibitors, there are concerns about adverse effects such as immunosuppression and liver dysfunction. In addition, hydroxymethylglutaryl coenzyme-A (HMG-CoA) reductase inhibitors (statin), angiotensin-converting enzyme inhibitors, angiotensin-receptor antagonists, and the like have been known to cause adverse effects such as poor appetite, nausea, vomiting, diarrhea, rash, and excessive hypotension.

Patent Document 1: JP Patent Publication (Kokai) No. 2007-106752 A

Patent Document 2: JP Patent Publication (Kokai) No. 9-110722 A (1997)

Patent Document 3: JP Patent No. 3954616

Non-Patent Document 1: Yasuaki Ogawa et al., Chem Pharm Bull 36: 2576-2581, 1988

Non-Patent Document 2: Tetsuo Hamano et al., Clinical Report 20: 5145-5154, 1986

Non-Patent Document 3: Koichi Yoshimura et al., Nature Medicine 11: 1330, 2005

Non-Patent Document 4: Resistant Bacterial Infectious Diseases: Theory and Practice (Taiseikin Kansensho no Riron to Jissai) edited by Keiichi Hiramatsu, Medical Journal Sha, Co., Ltd. (2002)

DISCLOSURE OF THE INVENTION

It is a main object of the present invention to provide a drug delivery system in which drugs can be changed or which can be recharged with drugs, which continuously delivers drugs at effective concentrations to local lesional sites in a body and allows the use of drugs for which it has thus far been difficult to achieve effective local concentrations for a variety of reasons and drugs which have been difficult to use due to adverse effects on tissues that are not sites of action.

The present inventors have found a method comprising inserting or implanting in vivo an indwelling medical device having target molecules on its surface and then administering, into a body, drug-encapsulated nanocarriers having target-recognizing molecules (e.g., bio-nanocapsules, liposomes, liposome preparations, polymeric micelles, and nanoparticles; hereinafter referred to as "nanocarriers"), thereby causing the nanocarriers to bind to the indwelling medical device via the target molecules and releasing a drug in the vicinity of an indwelling medical device as necessary. This has led to the completion of the present invention.

Specifically, the present invention provides (1) to (5) described below.

(1) A drug delivery system comprising an indwelling medical device having target molecules on its surface and target-recognizing nanocarriers in which drugs are encapsulated and which have target-recognizing molecules capable of specifically binding to the target molecules.

(2) The drug delivery system according to (1) above, wherein the indwelling medical device is coated with a biocompatible material and is targeted as a result of any of the following:

1) surface modification of the biocompatible material to bind appropriate target molecules thereto;

2) using the biocompatible material to which appropriate target molecules are pre-bound; and 3) using the biocompatible material to which appropriate functional groups are pre-bound and then appropriate target molecules that are designed to react with the functional groups are bound.

(3) The drug delivery system according to (1) or (2) above, wherein the target molecule presented on the indwelling medical device is selected from biotin which may be modified, glutathione which may be modified, a sugar which may be modified, and an epitope which may be modified.

(4) The drug delivery system according to any of (1) to (3) above, wherein the target-recognizing molecules carried by the drug-encapsulated target-recognizing nanocarriers as set forth in (1) above are designed to bind to the target molecules presented on the indwelling medical device as set forth in any of (1) to (3) above, thereby allowing the nanocarriers to bind to the indwelling medical device and then to cause sustained-release of the encapsulated drugs or to be introduced into surrounding tissues and to release the drugs.

(5) The drug delivery system according to any of (1) to (4) above, which is a system for use in the treatment of aneurysm, wherein the indwelling medical device is a stent graft and the target-recognizing nanocarriers in which drugs having JNK inhibitory activity are encapsulated are used.

According to the present invention, a therapeutic drug can be delivered to a lesion at a necessary point in time for a necessary period. Therefore, excellent therapeutic effects can be expected. Further, in a case in which undesirable adverse effects are observed after the initiation of sustained-drug release following which it is determined that disadvantages resulting from such undesirable adverse effects exceed benefits resulting from therapeutic effects of the drug, it can be expected that the drug dose can be reduced or the drug administration can be discontinued, allowing minimization of adverse effects. In addition, even in a case in which a sustained-released drug is in an unstable form and thus is inappropriate for long-term sustained-release, drug recharge is possible. In such a case, continuous drug delivery can be realized by repeating drug recharge within a period during which the drug activity is maintained.

This description incorporates the contents as disclosed in the claims, description and drawings of Japanese Patent Application No. 2007-331948 to which the present application claims priority.

BEST MODE FOR CARRYING OUT THE INVENTION

Figure 1:
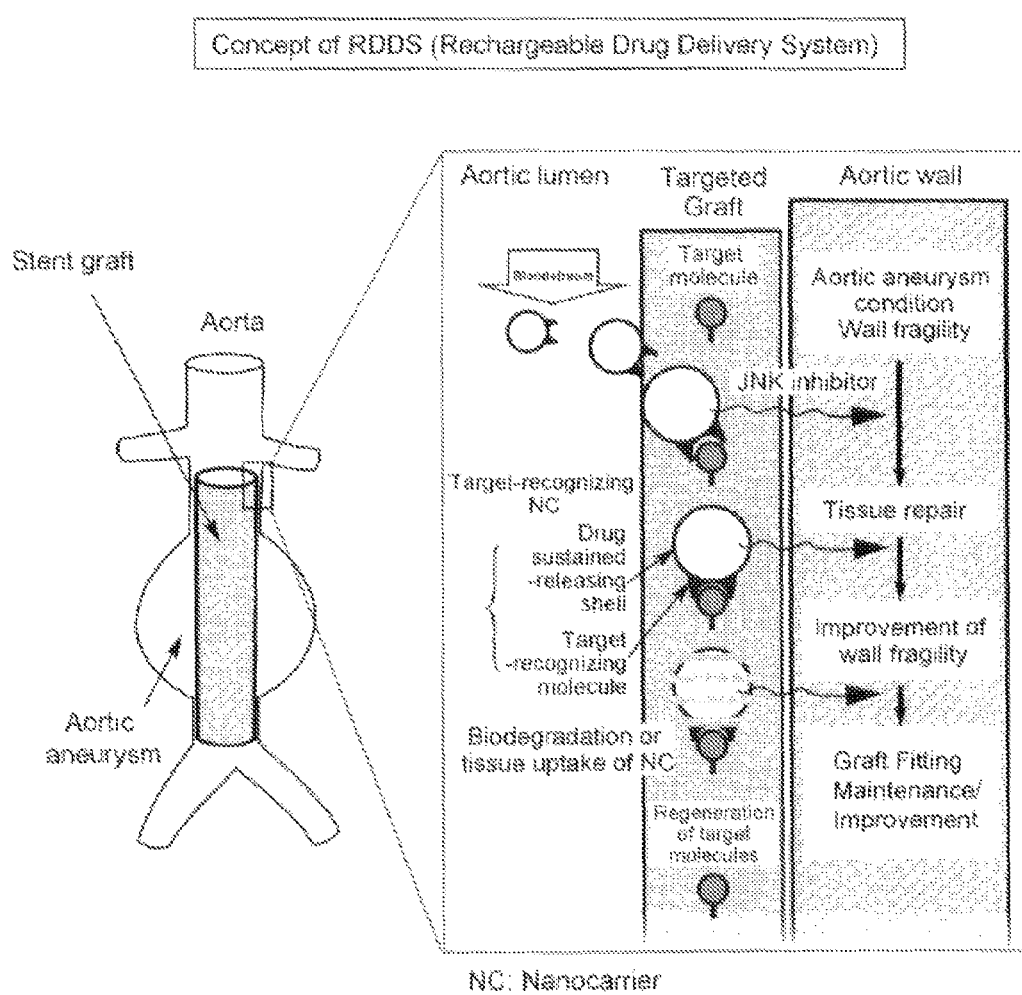
FIG. 1 is a conceptual diagram showing a rechargeable drug delivery system that is assumed to be used for aortic aneurysm treatment.

As shown in FIG. 1, the drug delivery system according to the present invention is a rechargeable drug delivery system, for example, for use in the treatment of aortic aneurysm, which is composed of a targeted graft (a targeted in vivo indwelling medical device) presenting appropriate target molecules on its surface and target-recognizing nanocarriers (preferably biodegradable target-recognizing nanocarriers), in which drugs are encapsulated, having target-recognizing molecules capable of binding to the target molecules on their surfaces. The drug delivery system according to the present invention can be provided in the form of a combination or kit for drug delivery.

An indwelling medical device according to the present invention is made of a highly biocompatible material. However, it is also possible to use a generally used indwelling medical device in a drug delivery system after targeting of such a device. Specifically, a targeted medical device is inserted and/or implanted into an appropriate site in a body, which enables the use of the device for releasing drugs in a body with charging the drugs more than once. Examples of such an indwelling medical device include stents (e.g., coronary artery vascular stents, brain stents, stents for the urethral opening, ureter stents, bile duct stents, tracheal stents, gastrointestinal stents, and esophageal stents), grafts, stent grafts, catheters, shunt tubes, intraocular lenses, intravascular coils, dental implants, indwelling needles for tumors, indwelling capsules for tumors, implantable defibrillators, heart valves, artificial pacemakers, artificial joints, artificial pleura, artificial dura mater, artificial bones, artificial pericardia, artificial inner ears, artificial cartilages, artificial hair, artificial retina, intravenous filters, venous valves, surgical suture staples, surgical sutures, and breast-enlargement inserts. Also, in vivo insertable and/or implantable medical devices used for cosmetic surgery can be included in the scope of the indwelling medical device of the present invention.

When the indwelling medical device is used for, for example, the treatment of aneurysm, a stent, a graft, a stent graft, or the like can be used. It is preferable to use, as such an indwelling medical device, a device that is made of a biocompatible material that has been currently used and has the size/shape appropriate for a relevant lesion.

Figure 2:
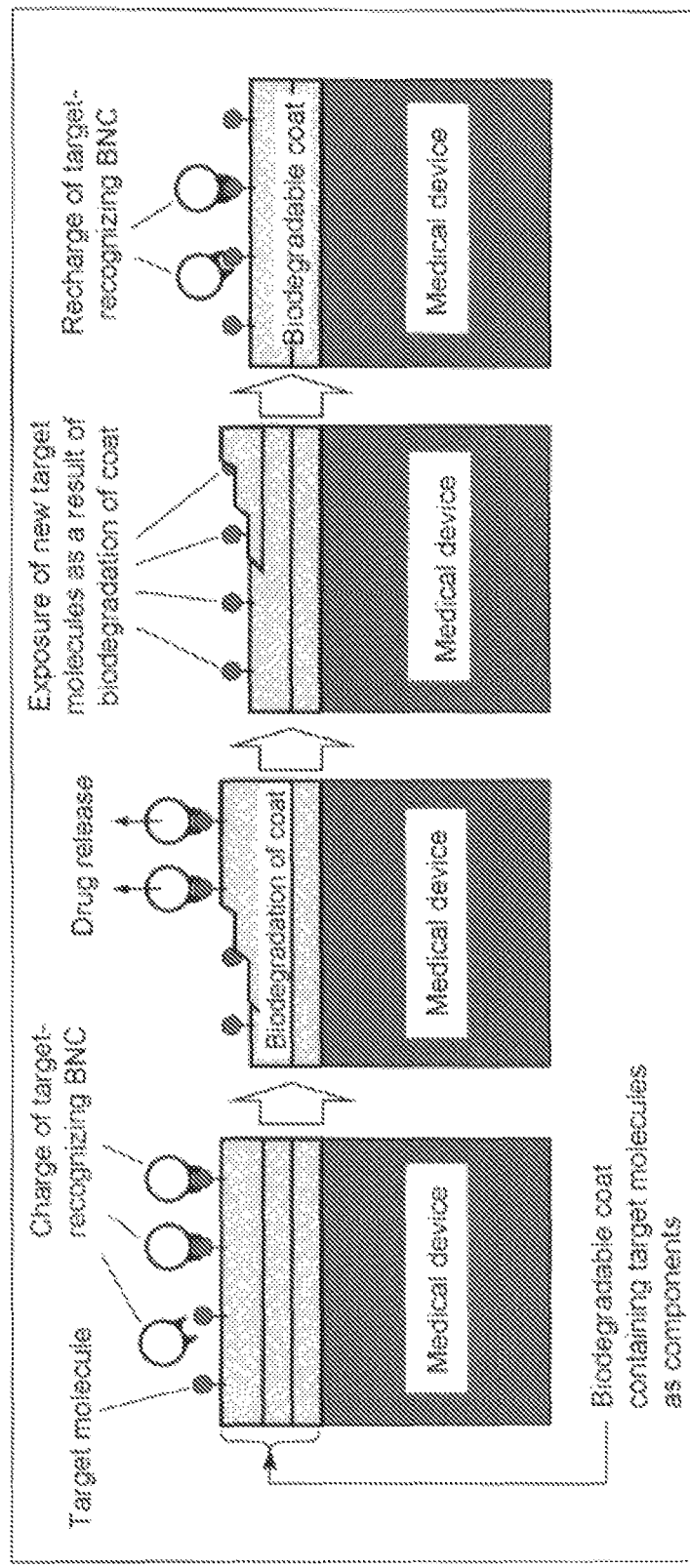
FIG. 2 is a conceptual diagram showing the process of exposure of new target molecules as a result of gradual degradation of the surface of an indwelling medical device coated with a biodegradable material having target molecules.

The indwelling medical device is preferably coated with a biocompatible material. Such biocompatible material may be a biodegradable material. Examples of biodegradable material include aliphatic polyester, polyvinyl alcohol, polyglycolic acid, polylactic acid (PLA)/polycaprolactone (PCL), polyester-based polyamino acid, polypeptide, polydepsipeptide, nylon copolyamide, starch, cellulose, collagen, hyaluronic acid, alginic acid, chitin, and chitosan. When a biodegradable material is used, target molecules embedded in a coating material can be newly exposed as a result of degradation of the surface of the indwelling medical device (FIG. 2). This is one embodiment of the present invention.

In general, in the case of an in vivo insertable and/or implantable medical device (indwelling medical device), the device surface is coated with a biocompatible material in order to enhance biocompatibility. As a biocompatible material used for coating of the device surface, a highly biocompatible polymeric material can be used. Examples of highly biocompatible polymeric material include: polyolefins (e.g., polyethylene, polyisoprene, and polypropylene) and copolymers thereof; polyesters (e.g., polyethylene terephthalate, polyethylene naphthalate, and polybutylene naphthalate); acrylate-based polymers (e.g., polymethylmethacrylate, polyhydroxyethyl methacrylate, and polymethoxyethylacrylate); cellulose-based polymers (e.g., cellulose acetate and cellulose nitrate); polytetrafluoroethylene; polyurethane; methyl methacrylate; 2-hydroxyethyl methacrylate; collagen; chitin; and chitosan.

The indwelling medical device according to the present invention can be targeted by allowing a material (to be coated) to present appropriate molecules. (Hereinafter, a targeted indwelling medical device having target molecules on its surface is also referred to as a targeted medical devices.) Examples of a targeting method in one embodiment include: a technique involving binding appropriate molecules for targeting to a relevant material having biocompatibility by surface modification of the material; a technique involving pre-binding appropriate molecules for targeting to a relevant material having biocompatibility to be used; and a technique involving pre-binding appropriate functional groups to a relevant material having biocompatibility to be used and then pre-binding appropriate molecules for targeting that have been designed to react with the functional groups thereto. It is desirable to appropriately select such a technique depending on physical and chemical properties of a relevant material having biocompatibility and target molecules and also depending on lesions to be treated. In the present invention, the term "material having biocompatibility" and the term "biocompatible material" can be interchangeably used.

A combination of molecules used for target recognition for medical device targeting (a combination of a target molecule and a target-recognizing molecule) is not particularly limited. However, examples of such combination include a combination of biotin and avidin, a combination of biotin and streptavidin, a combination of biotin and NeutrAvidin®, a combination of biotin and human-derived biotin-binding molecules, a combination of biotin and Strep-Tactin®, a combination of Strep-Tag® and Strep-Tactin®, a combination of Strep-TagII® and Strep-Tactin®, a combination of S-Tag® and S-protein, a combination of Halo Ligand® and Halotag®, a combination of glutathione and glutathione S-transferase, a combination of amylose and a maltose-binding protein, a combination of appropriately designed epitope and a humanized monoclonal antibody for the epitope, and a combination of appropriately designed sugar chains and relevant sugar chain-recognizing molecules including lectin and humanized monoclonal antibodies. Herein, biotin, glutathione, a sugar, an epitope, or the like may be modified with a spacer arm (e.g., polyethylene glycol or hydrocarbon) and a reaction group (e.g., an N-hydroxysuccinimide group, a sulfo-N-hydroxysuccinimide group, a pentafluorophenyl group, a hydrazide group, an amide group, a pentylamine group, a maleimide group, a hexyl(pyridyldithio)propionamide group, a iodoacetyl group, a ridyl group, an azidosalicylamide group, a nitrophenyl azide group, a psoralen group, or a tetraphenylfluoroazido group). Also, a combination of nucleic acid and a relevant nucleic acid complementary thereto, a combination of an antigen and an antibody or a fragment thereof, a combination of an enzyme and a substrate or an inhibitor, and a combination of a ligand and a receptor can be used. As molecules (target molecules) to be presented on the targeted medical device surface, molecules that are stable under in vivo conditions are selected.

The nanocarriers (target-recognizing nanocarriers) of the present invention include bio-nanocapsules, liposomes, liposome preparations, polymeric micelles, and nanoparticles. The nanocarriers have target-recognizing molecules that recognize a targeted medical device and function as drug release portions. A complex of a drug and a nanocarrier can be prepared by any one selected from the following methods: 1) a method involving binding a drug to a water-soluble polymer; 2) a method involving embedding a drug in a nano-size fine particle; 3) a method involving allowing a drug to be mixed with or encapsulated in a vesicle composed of a lipid bilayer membrane that corresponds to an artificial cellular membrane, which is called "liposome"; 4) a method involving allowing a drug to be encapsulated in an assembly of polymers having inhomogeneous structures, which is called "polymeric micelle"; and 5) a method involving allowing a drug to be encapsulated in a nano-size biocapsule (bio-nanocapsule).

The target-recognizing nanocarriers of the present invention can contain a single drug or multiple drugs in the same population or different populations of the nanocarriers. Such nanocarriers are degraded, which results in sustained-release of encapsulated drugs. As a result, therapeutic effects can be expected to be obtained.

Alternatively, therapeutic effects can be expected when such nanocarriers are introduced in vivo and bind to target molecules on a targeted medical device, followed by being introduced into a surrounding tissue, which results in drug release.

Bio-nanocapsules used in the present invention are nano-size capsules produced by a genetically engineered microorganism. It is possible to use, as a bio-nanocapsule, a virus protein-derived or modified virus protein-derived particle, such as a virus surface antigen particle (e.g., a hepatitis B virus surface antigen (HBsAg) particle). It is also possible to use, as a bio-nanocapsule, a nano-size capsule comprising a lipid bilayer membrane and a virus protein-derived or modified virus protein-derived particle such as a virus surface antigen particle (e.g., a hepatitis B virus surface antigen (HBsAg) particle). Such particles can be purified from eukaryotic cells such as yeasts, insect cells, and mammalian cells. The size of a capsule that can be used is approximately 10 nm to 500 nm, preferably 20 nm to 250 nm, and most preferably 80 nm to 150 nm can be used.

In addition, a technique of fusing liposomes and bio-nanocapsules with high efficiency while maintaining their characteristics has been known in the art. Drug-encapsulated target-recognizing nanocarriers can be readily produced via fusion of drug-encapsulated liposomes and target-recognizing bio-nanocapsules (Journal of Controlled Release 126 (2008) 255-264).

In a general embodiment of the drug delivery system, a targeted medical device is inserted or implanted beforehand in a body and then target-recognizing nanocarriers are administered in the body at any point in time. As an administration route, a route that most facilitates target-recognizing nanocarriers to reach a targeted medical device is selected.

For instance, in a case in which a targeted medical device is placed in a blood vessel, it is appropriate to administer target-recognizing nanocarriers into the blood vessel. In a case in which a targeted medical device is placed in the digestive tract, it is appropriate to orally administer target-recognizing nanocarriers. In a case in which a targeted medical device is exposed in or located close to a body cavity such as the pericardial cavity, the thoracic cavity, the peritoneal cavity, or the cerebrospinal cavity, it is appropriate to administer target-recognizing nanocarriers into such body cavity. In a case in which a targeted medical device is located closed to the living body surface, it is appropriate to administer target-recognizing nanocarriers in the vicinity of the medical device via subcutaneous injection or the like. Basically, it is desired that the above administration method be appropriately selected in view of the type of lesion to be treated by the medical device and diagnostic effects and/or therapeutic effects that are expected to be obtained by the present invention.

The present invention can be applied to any disease for which a medical device needs to be inserted or to be placed in vivo. Examples of a combination of a target disease and a medical device are described below:

grafts, stent grafts, and intravascular coils for aneurysms such as aortic aneurysms;

stents, stent grafts, and grafts for dilation, stenosis, occlusion, and the like of blood vessels such as the coronary artery;

stents, stent grafts, and grafts for stenosis, occlusion, deficiency, and the like of respiratory tracts (e.g., larynx, trachea, and bronchi), urethra, ureter, and digestive tracts (e.g., bile duct, pharynx, esophagus, stomach, and intestine);

catheters for conditions that require tube feeding or intravenous feeding such as inflammatory intestine diseases, conditions after digestive tract excision, malnutrition, and disturbed consciousness;

shunt tubes for hydrocephalus and the like;

intraocular lenses for cataract, ocular trauma, and the like;

dental implants for dental conditions such as dental physical damage, decay, odontoma, odontogenic myxoma, odontogenic cyst, apical cyst, pulpitis, pulp disease, pulp hyperemia, odontogenic maxillary sinusitis, and dens invaginatus;

drug release devices comprising tissue-indwelling needles, capsules, mesh, or the like for local lesions such as general tumors, cysts, central nerve diseases, peripheral nerve diseases, and the like;

implantable defibrillators and artificial pacemakers for cardiomyopathy, arrhythmia, heart failure, and the like;

heart valves for congenital cardiovascular malformation, cardiac valvular diseases, and the like;

artificial joints for arthritis such as rheumatoid arthritis, joint trauma, or the like;

artificial pleura used after the surgery of chest region and the like;

artificial dura mater used after the brain surgery and the like;

artificial bones used after the surgery for bone trauma, bone tumors, and the like;

artificial pericardia used after the surgery for large blood vessels of the heart or the like;

artificial inner ears for inner ear diseases and the like;

artificial cartilages used for the surgery of trauma, tumor, or the like, or for arthritis such as rheumatoid arthritis, joint trauma, or the like;

artificial hair for skin trauma, skin burn, dermatitis, alopecia, or the like;

artificial retina for retina diseases (e.g., etinitis pigmentosa, macular degeneration, glaucoma, retinal hemorrhage, and fundal hemorrhage) and ocular trauma;

intravenous filters and venous valves for venous diseases such as venous thrombosis, venous inflammation, and varix;

surgical suture staples used for diseases that require digestive tract anastomosis, blood vessel anastomosis, or the like;

surgical sutures used for general surgery and the like; and in vivo insertable and/or implantable prosthesis and the like used for cosmetic surgery and the like.

In a case in which an intravascular stent graft is used as a targeted medical device for the treatment of aneurysm, target-recognizing nanocarriers in which aneurysm therapeutic drugs are encapsulated are administered inside a blood vessel. A stent graft is a medical instrument obtained by sewing a self-expandable stent with an artificial blood vessel (graft). Such a stent graft is designed to extend through an aneurysm artery portion so as to reach normal vascular sites existing in front and to the rear of an aneurysm. Such a stent graft inserted inside the aneurysm portion expands by itself, tightly adheres to normal vascular sites located in front and to the rear of the aneurysm, and cuts off the hemodynamic load on the aneurysm so as to cause therapeutic effects. Since intravascular treatment with the use of stent grafts is less invasive than surgery, the treatment has been gaining preference.

In an embodiment based on stent graft treatment for aneurysm, the following drugs can be encapsulated in target-recognizing nanocarriers. Specifically, the drugs are: MMP inhibitors including tetracycline derivatives such as doxycycline; antibiotics such as roxithromycin; chemokine antagonists such as macrophage chemotactic factors (Monocyte chemocttractant protein: MCP-1) and/or receptor (CCR2) antagonists thereof; TNF-α, IL-6, IL-1β, INF-γ, and/or receptor antagonists thereof; TGF-β and/or receptors thereof; SMAD antagonists; angiotensin II receptor antagonists; angiotensin-converting enzyme (ACE) inhibitors; renin inhibitors; arachidonic acid-5-lipoxygenase inhibitors; cyclooxygenase inhibitors; non-steroidal anti-inflammatory drugs (NSAID) such as aspirin; antioxidant drugs such as nitrogen monoxide synthase inhibitors, vitamin E, vitamin C, and derivatives thereof; immunosuppressants such as steroids, rapamycin, and cyclosporine A; elastin-stabilizing agents such as elastin-binding polyphenol pentagalloylglucose; JNK inhibitors; NFκB inhibitors such as oligo DNA (decoy) having a binding site of an NFκB and/or Ets transcription factor; and HMG-CoA reductase inhibitors (statin). It is possible to select and encapsulate one or more member of the above examples.

Further, in the present invention, when using an indwelling stent for the coronary artery as a targeted medical device used for diseases accompanied with coronary artery stenosis, a therapeutic drug to be encapsulated in target-recognizing nanocarriers can be selected as follows. Specifically, it is possible to select for encapsulation one or more anti-restenosis drug(s) such as paclitaxel, heparin, sirolimus, everolimus, tacrolimus, dexamethasone, estradiol, trapidil, dactinomycin, clopidogrel, and ridogrel.

Nanocarriers are superior to conventional drug delivery carriers in terms of a function of intracellularly delivering substances. Therefore, nanocarriers are particularly excellent as carriers capable of delivering broad categories of drugs having different physical properties. In the present invention, for the purpose of applying to other lesions, drugs to be used can be, but not limited to, any one selected, as therapeutic drugs to be encapsulated in target-recognizing nanocarriers, from the following: heparin; low-molecular-weight heparin; heparinoids such as dextran sulfate and β-cyclodextrin tetradecasulfate; heparin derivatives; urokinase; RGD peptide-containing compound; antithrombin compounds such as hirudin, hirulog, and argatrob an; platelet receptor antagonists; antithrombin antibodies, antiplatelet receptor antibodies, aspirin; prostaglandin inhibitors and antiplatelet peptides; GPIIb and IIIa inhibitors such as ticlopidine, clopidogrel, abciximab, eptifibatide, and tirofiban; FXa inhibitors; anticoagulants such as vitamin K inhibitors (e.g., warfarin); antithrombotic agents; platelet agents; platelet adhesion inhibitors such as albumin and polyethylene oxide; cyclooxygenase pathway inhibitors such as aspirin, ibuprofen, flurbiprofen, indomethacin, and sulfinpyrazone; lipoxygenase pathway inhibitors; leukotriene receptor antagonists; thromboxane A2 (TAX2) pathway modifiers such as sulotroban, vapiprost, dazoxiben, and ridogrel; natural and synthetic adrenal cortical steroids such as dexamethasone, prednisolone, corticosterone, methoprednisolone, and hydrocortisone; estrogen; anti-inflammatory drugs (e.g., sulfasalazine and mesalamine), antitumor agents, antiproliferative drugs, mitotic division inhibitors, cell-division-arresting agents, and cell-proliferation-influencing factors (e.g., paclitaxel, 5-fluorouracil, cisplatin, vinblastine, vincristine, epothilone, endostatin, angiostatin, angiopeptin, monoclonal antibodies capable of blocking smooth muscle cell proliferation, and thymidine kinase inhibitors); cell cycle inhibitors such as CDK inhibitors; tyrosine kinase inhibitors (e.g., tyrphostin, genistein, and quinoxaline derivatives) and other protein kinase inhibitors; purine analogs (cladribine that is a 6-mercaptopurine or chlorinated purine nucleotide analog); metabolic antagonists such as pyrimidine analogs (e.g., cytarabine and 5-fluorouracil) and methotrexate; antitumor antibiotics such as nitrogen mustard, alkyl sulfonic acid, ethyleneimine, daunorubicin, and doxorubicin; drugs that influence microtubule movement such as nitrosourea, cisplatin, vinblastine, vincristine, colchicine, paclitaxel, and epothilone; angiogenesis inhibitors such as caspase activators, proteasome inhibitors, endostatin, and angiostatin; antiproliferative and antitumor agents (e.g., rapamycin, cerivastatin, flavopiridol, and suramin); vascular cell growth inhibitors such as growth factor inhibitors, growth factor receptor antagonists, antibodies antagonistic to growth factors, transcription repressors, translation repressors, replication inhibitors, antibodies capable of recognizing endothelial progenitor cells, bifunctional molecules comprising growth factors and cytotoxin, and bifunctional molecules comprising antibodies and cytotoxin; cytokine and hormone; acidic and basic fibrous cell growth factors; FGF pathway drugs such as bFGF antibodies and chimeric fusion proteins; angiogenesis factors such as growth factors (e.g., angiopoietin, vascular endothelial growth factors, endothelial division promotion (growth) factors, epithelial growth factor, transforming growth factors α and β, platelet-derived endothelial growth factors, platelet-derived growth factors, tumor necrosis factor α, hepatocellular growth factors, and insulin-like growth factors); endothelialization-promoting agents such as RGD peptide; PDGF receptor antagonists such as trapidil; IGF pathway drugs such as somatostatin analogs (e.g., angiopeptin and octreotide); polyanion reagents (e.g., heparin and fucoidan); TGF-β pathway drugs such as decorin and TGF-β antibodies; EGF pathway drugs such as EGF antibodies; TNF-α pathway drugs such as receptor antagonists, chimeric fusion proteins, and thalidomide and analogs thereof; adenylate and guanylate cyclase stimulants such as forskolin; cyclic nucleotide pathway drugs such as phosphodiesterase inhibitors (e.g., cilostazol and dipyridamole); calcium channel blockers such as benzothiazepine (e.g., diltiazem), dihydropyridine (e.g., nifedipine, amlodipine, and nicardipine) and phenylalkylamine (e.g., verapamil); serotonin pathway modifiers such as 5-HT antagonists (e.g., ketanserin and naftidrofuryl) and 5-HT absorption inhibitors (e.g., fluoxetine); catecholamine modifiers such as α antagonists (e.g., adenosine analogs, prazosin, and bunazosin), β antagonists (e.g., propranolol), and α and β antagonists (e.g., labetalol and carvedilol); endothelin receptor antagonists; ACE inhibitors such as cilazapril, fosinopril, and enalapril; endogenous vasoactive mechanism inhibitors such as angiotensin-receptor antagonists (e.g., saralasin, losartan, candesartan, and valsartan); other vasodilators such as hydralazine; adrenaline α agonists; adrenaline β agonists; dopamine agonists; prostaglandins, analogs thereof, and prostacyclin analogs such as prostaglandins E1, E2 and I2; organic nitrates and nitrites such as nitroglycerin, isosorbide dinitrate, and amyl nitrite; inorganic nitroso compounds such as sodium nitroferricyanide(III) dehydrate; sydnonimines such as molsidomine and linsidomine; nitrogen monoxide adducts such as diazeniumdiolate and alkanediamine; S-nitroso compounds containing low-molecular-weight compounds (e.g., S-nitroso derivatives of captopril, glutathione, and N-acetylpenicillamine) and S-nitroso compounds containing high-molecular-weight compounds (e.g., S-nitroso derivatives of proteins, peptides, oligosaccharides, polysaccharides, synthetic polymers, or oligomers and natural polymers or oligomers); nitrogen monoxide donors and nitrogen monoxide-releasing molecules such as C-nitroso compounds, O-nitroso compounds, N-nitroso compounds, and L-arginine; E- and P-selectin antagonists; VCAM-1-ICAM-1 interaction inhibitors; macrophage activation inhibitors such as bisphosphonate; cholesterol-lowering agents such as HMG-CoA reductase inhibitors (e.g., lovastatin, pravastatin, fluvastatin, simvastatin, cerivastatin, and pitavastatin); fish oil and omega-3-fatty acid; radical scavenger antioxidants such as probucol, vitamins C and E, ebselen, and trans retinoic acid; anesthetic drugs such as lidocaine, bupivacaine, and ropivacaine; MMP pathway inhibitors such as marimastat, ilomastat, and metastat; cell movement inhibitors such as cytochalasin B; matrix deposition and assembly pathway inhibitors such as quinazolinone derivatives (e.g., halofuginone) and tranilast; hemorheology modifiers such as pentoxifylline; triclosan; antimicrobial agents such as nitrofurantoin; penicillin antibiotics such as sultamicillin, amoxicillin, aspoxicillin, and piperacillin; cephalosporin antibiotics such as cefaclor, cefazolin, cefotiam, flomoxef, cefteram, ceftazidime, cefmenoxime, cefozopran, and cefsulodin; carbapenem antibiotics such as imipenem, panipenem, and meropenem; monobactam antibiotics such as aztreonam; aminoglycosides such as amicacin, dibekacin, tobramycin, teicoplanin, streptomycin, and gentamicin; synthetic antimicrobial agents such as polymixin B, vancomycin, nalidixic acid, ofloxacin, ciprofloxacin, tosufloxacin, levofloxacin, and fosfomycin; macrolide antibiotics such as erythromycin, clarithromycin, roxithromycin, and azithromycin; lincomycin antibiotics such as clindamycin and lincomycin; tetracycline antibiotics such as doxycycline and minocycline; antibiotics and antimicrobial agents such as chloramphenicol, thiamphenicol, sulfurmethoxyn, and sulfurmethoxazole; antituberculous agents such as isoniazid, rifampicin, and ethambutol; antileprotics such as diaphenylsulfone and clofazimine; antifungal agents such as nystatin, miconazole, metronidazole, fluconazole, amphotericin B, and clotrimazole; antiviral agents such as ganciclovir, oseltamivir, vidarabine, aciclovir, and palivizumab; and antiprotozoal agents such as pentamidine.

Further, examples of drugs to be encapsulated in the target-recognizing nanocarriers of the present invention that can be used include low-molecular inorganic compounds, low-molecular organic compounds, polymeric inorganic compounds, polymeric organic compounds, peptides, and nucleic acids. Examples of peptides that can be used include a peptide having biological molecule activation or inhibitory action. Examples of nucleic acids encoding peptides or nucleic acids that can be used include a nucleic acid encoding a peptide having biological molecule activation or inhibitory action, interference RNA for biological molecules, a ribozyme, an antisense nucleic acid, and a nucleic acid encoding any of such examples. In addition, a peptide or a nucleic acid capable of controlling transcription or translation of biological molecules and a nucleic acid encoding such peptide or nucleic acid can be used.

In addition, the present invention relates to a drug delivery method using the drug delivery system as mentioned above. The drug delivery method according to the present invention comprises allowing an indwelling medical device having target molecules on its surface to indwell (be inserted) in a body and administering target-recognizing nanocarriers carrying target-recognizing molecules capable of specifically binding to the target molecules, in which drugs are encapsulated. Such an indwelling medical device and target-recognizing nanocarriers are as described above in the section of the drug delivery system.

Also, a combination of a disease to which the drug delivery method of the present invention is applied and a medical device is as described above in the section of the drug delivery system. Persons skilled in the art can select the type of indwelling medical device and the in vivo site for indwelling (insertion) based on a relevant disease. Examples of the in vivo site for indwelling of an indwelling medical device include blood vessels, respiratory tracts (e.g., larynx, trachea, and bronchi), urethra, ureter, digestive tracts (e.g., bile duct, pharynx, and esophagus/stomach/intestine), eyes, oral cavity, teeth, tumors, cysts, central nerves, peripheral nerves, heart, joints, the chest region, the cephalic region, bones, inner ears, and skin.

In one embodiment, the drug delivery method of the present invention comprises placing a targeted medical device in a blood vessel and administering target-recognizing nanocarriers into the blood vessel. In another embodiment, the drug delivery method of the present invention comprises placing a targeted medical device in the digestive tract and orally administering target-recognizing nanocarriers. In another embodiment, the drug delivery method of the present invention comprises placing the targeted medical device in a living body cavity such as the pericardial cavity, the thoracic cavity, the peritoneal cavity, or the cerebrospinal cavity in a manner such that the device is exposed in or located close to such cavity and administering target-recognizing nanocarriers into such body cavity. In another embodiment, the drug delivery method of the present invention comprises placing a targeted medical device in the vicinity of the living body surface and administering target-recognizing nanocarriers in the vicinity of the medical device via subcutaneous injection or the like.

Preferably, subjects to which the drug delivery system and the drug delivery method of the present invention can be applied are mammals. Examples of mammals include warm-blooded vertebrates such as primates (e.g., humans and monkeys), rodents (e.g., mice, rats, and rabbits), pet animals (e.g., dogs and cats), and livestock (e.g., bovine, horses, and pigs).

EXAMPLES

Hereinafter, for the purpose of explaining the present invention in more detail, Examples showing the targeting of an indwelling medical device with the use of biotin as a target molecule, avidin as a target-recognizing molecule, and a Dacron® artificial blood vessel as an example device are described below. However, the present invention is not limited thereto.

Example 1

Biotinylation of Dacron Artificial Blood Vessel (Graft) Surface and In Vitro Detection of Biotin

Figure 3:
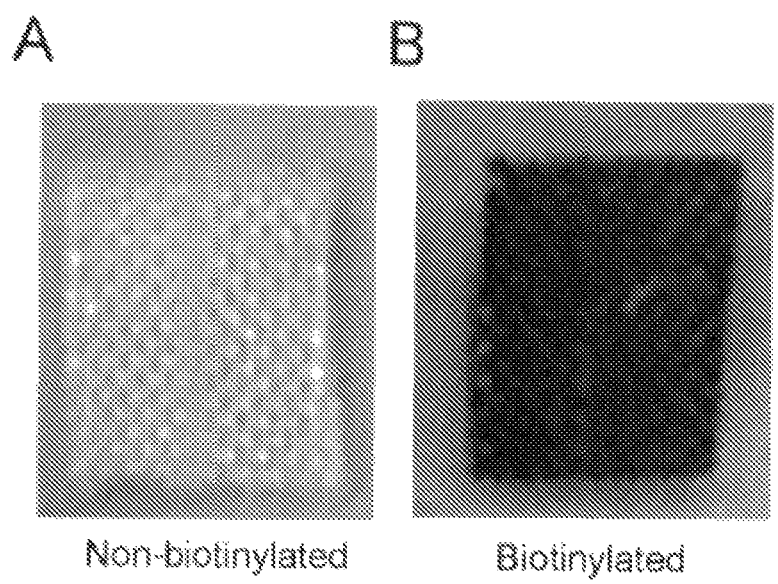
FIG. 3 shows photographs as a substitute for diagrams that indicate the observation of biotinylation on the surface of a Dacron artificial blood vessel (A, Non-biotinylated; B, Biotinylated).

[Method]
The surface of a Dacron artificial blood vessel (UBE woven Graft®: Ube Industries, Ltd.) was treated with 1N sodium hydroxide to partially hydrolyze it so as to expose free carboxyl groups. A surface-biotinylated graft was prepared with the use of 1-ethyl-3-(3-dimethylaminopropyl)carbodiimide hydrochloride as a cross-linker and EZ-Link® Biotin-PEO3-LC Amine (Pierce). As a control, a graft was prepared by carrying out partial hydrolysis of the surface without biotinylation. An avidin-alkaline phosphatase complex was formed beforehand by mixing avidin and biotinylated alkaline phosphatase in a test tube (VECTASTAIN® ABC-AP KIT, Vector Laboratories). Each graft was sufficiently washed and then reacted with the avidin-alkaline phosphatase complex, followed by detection of biotin on the graft surface by a so-called ABC method.
[Results]
Red color development using the alkaline phosphatase reagent (VECTOR RED®: Vector Laboratories) was observed only on the biotinylated graft. This demonstrated the biotinylation of the graft surface (FIG. 3).

Example 2

Biotinylation of Collagen-Coated Artificial Blood Vessel (Graft) Surface and In Vitro Detection of Biotin

Figure 4:
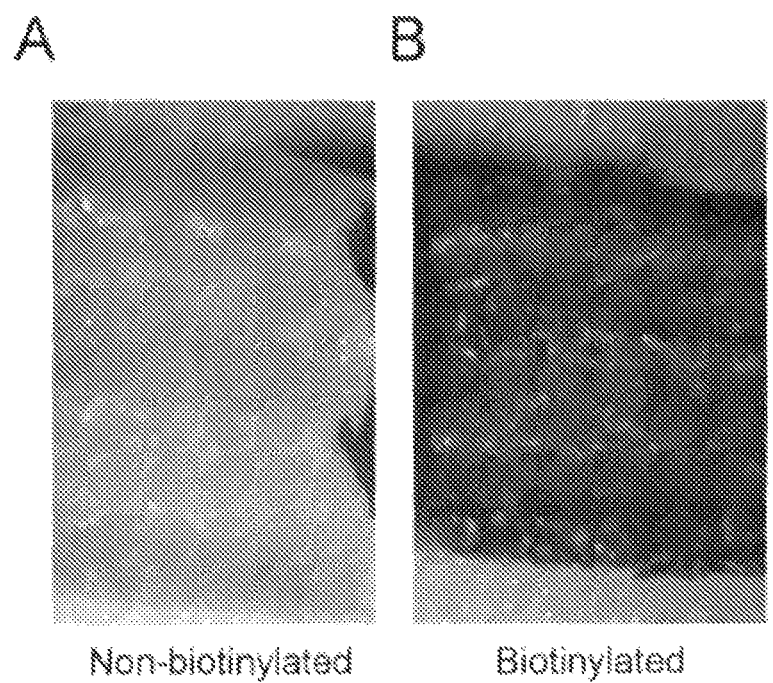
FIG. 4 shows photographs as a substitute for diagrams that indicate the observation of biotinylation on the surface of the collagen-coated surface of a Dacron artificial blood vessel (A, Non-biotinylated; B, Biotinylated).

[Method]
A surface-biotinylated graft was prepared by allowing EZ-Link® NHS-LC-Biotin (Pierce) to act on a Dacron artificial blood vessel (Hemashield®, Boston Scientific) coated with collagen for the improvement of biocompatibility. A control graft was prepared without biotinylation. An avidin-alkaline phosphatase complex was formed beforehand by mixing avidin and biotinylated alkaline phosphatase in a test tube (VECTASTAIN® ABC-AP KIT, Vector Laboratories). Each graft was sufficiently washed and then reacted with the avidin-alkaline phosphatase complex, followed by detection of biotin on the graft surface by the ABC method.
[Results]
Red color development using the alkaline phosphatase reagent (VECTOR RED®, Vector Laboratories) was observed only on the biotinylated graft. This demonstrated the biotinylation of the graft surface (FIG. 4).

Example 3

Verification of In Vivo Binding of Avidin to a Surface-Biotinylated Artificial Blood Vessel (Graft)

[Method]
A surface-biotinylated graft was prepared by allowing EZ-Link® NHS-LC-Biotin (Pierce) to react on a Dacron artificial blood vessel (Hemashield®, Boston Scientific) coated with collagen for the improvement of biocompatibility. A control graft was prepared without biotinylation. Each graft was sufficiently washed. Thereafter, both the biotinylated graft and the untreated graft were implanted inside the inferior vena cava of the same mouse. An avidin-alkaline phosphatase complex was formed beforehand by mixing avidin and biotinylated alkaline phosphatase in a test tube. The avidin-alkaline phosphatase complex was intravenously administered to the mouse subjected to the graft implantation. Thirty minutes later, the mouse was sacrificed and the grafts inside the inferior vena cava were excised. The grafts were reacted with an alkaline phosphatase color-developing reagent (VECTOR RED®, Vector Laboratories). Red fluorescence of VECTOR RED was observed with a laser scanning confocal microscope to verify whether alkaline phosphatase was bound to biotin present on the graft fiber bundle surface.

Figure 5:
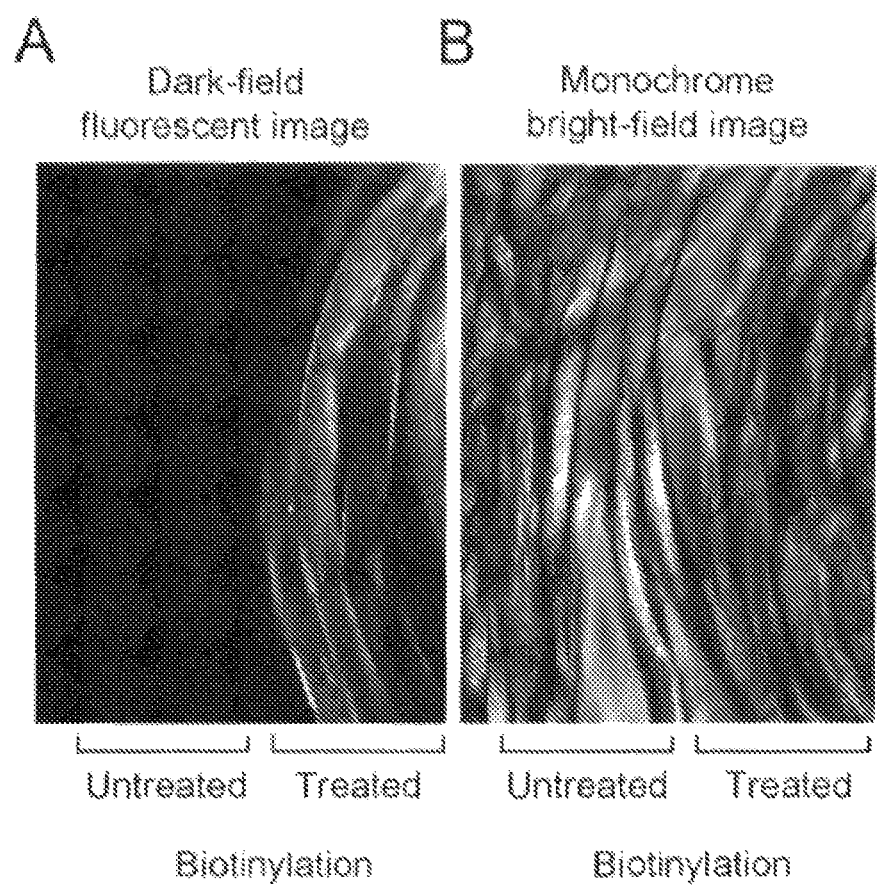
FIG. 5 shows photographs as a substitute for diagrams that indicate the specific binding of an avidin-alkaline phosphatase complex to a biotinylated graft also under in vivo conditions (A, dark-field fluorescent image; B, monochrome light-field image).

[Results]
Red fluorescence of VECTOR RED was strongly observed only on the biotinylated graft. Meanwhile, no fluorescence was observed on the untreated graft. This demonstrated that an avidin-alkaline phosphatase complex specifically binds to a biotinylated graft even under in vivo conditions (FIG. 5).

Example 4

Drug Encapsulation in Liposomes

A JNK inhibitor (SP600125) and statin (Pitavastatin), which are assumed to be used as therapeutic drugs for aortic aneurysm, were encapsulated in liposomes in accordance with the procedures described below.
1) Lipids were dissolved in a methanol/chloroform (1:1) solution (2 ml) (total lipids: mg; DPPC:DPPE:DPPG:cholesterol=15:15:40:30) (DPPC: dipalmitoylphosphatidylcholine; DPPE: dipalmitoylphosphatidylethanolamine; and DPPG: dipalmitoylphosphatidylglycerol).
2) The drug (0.5 mg) was dissolved in the above solution.
3) The solvent was evaporated using an evaporator with heating in a water bath at 60° C. to prepare a lipid film.
4) The film was hydrated with a buffer (10 mM HEPES, 150 mM NaCl, pH 7.4) (1 ml).
5) The hydrated film was passed through an extruder (Avestin, 500 ml syringe-type, pore size: 100 nm) 50 times such that the particle size was adjusted.
6) Gel filtration (Superdex G-50) was carried out to remove unencapsulated drugs, and thus purified liposomes were obtained.

SP600125 and Pitavastatin each exhibited specific fluorescence characteristics. Accordingly, it was confirmed that they can be quantified by fluorescence photometry. Purified liposomes were destroyed in the presence of 0.1 N HCl and 0.5% SDS for fluorescence measurement of released drugs. The lipid content was calculated based on the DPPC content determined with the use of phospholipid C-Test Wako (Wako Pure Chemical Industries, Ltd.). The particle size was determined by a dynamic light scattering method. Table 1 shows the results.

TABLE 1

|  | SP600125-containing liposome | Pitavastatin-containing liposome | Conventional liposome |
| --- | --- | --- | --- |
| Lipid concentration (mg/ml) | 204 | 198 | 199 |
| Drug concentration (mg/ml) | 620 | 75.5 | — |
| Particle size (nm, as Z-average) | 220 (PDI: 0.420) | 150 (PDI: 0.341) | 137 (PDI: 0.232) |
| Drug content per 1 mg of lipid (mg) | 3.04 | 0.381 | — |
| Drug content per 1 mg of lipid (mmol) | 13.8 | 0.432 | — |
| Estimated encapsulatable content (in 10 mg lipid/ml soln.) | 138 mM | 4.32 mM | — |

The results shown in Table 1 indicate that Pitavastatin and SP600125 can be encapsulated in liposomes at high concentrations.

Example 5

Targeted Graft and Target-Recognizing Nanocarriers

Figure 6:
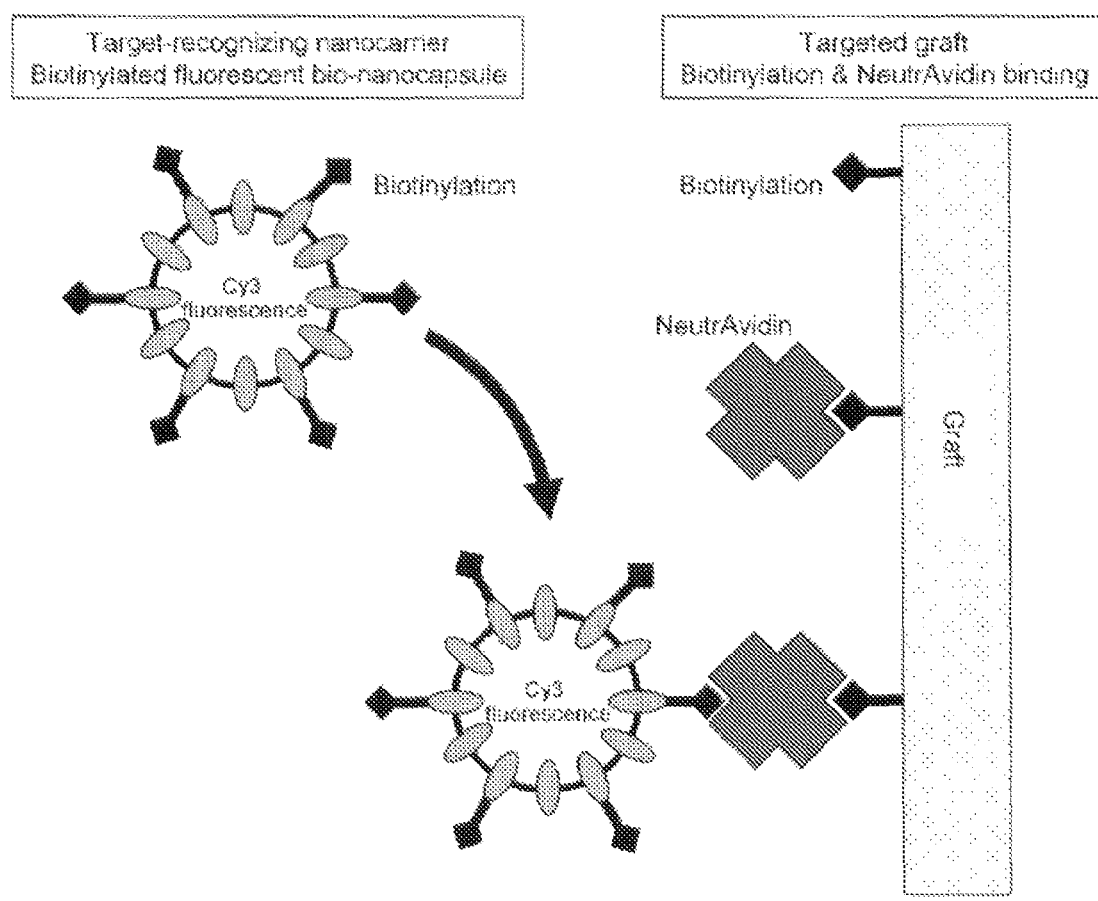
FIG. 6 is a conceptual diagram showing a targeted graft and bio-nanocapsules used for demonstration experiments.

FIG. 6 shows a conceptual diagram of a targeted graft and bio-nanocapsules used in demonstration experiments. A targeted graft was prepared by binding neutravidin to the biotinylated graft shown in FIG. 3. Target-recognizing nanocarriers were prepared by biotinylating Cy3-fluorescent labeled bio-nanocapsules (nano-size capsules each comprising particles from a modified hepatitis B virus surface antigen and a lipid bilayer membrane).

Figure 7:
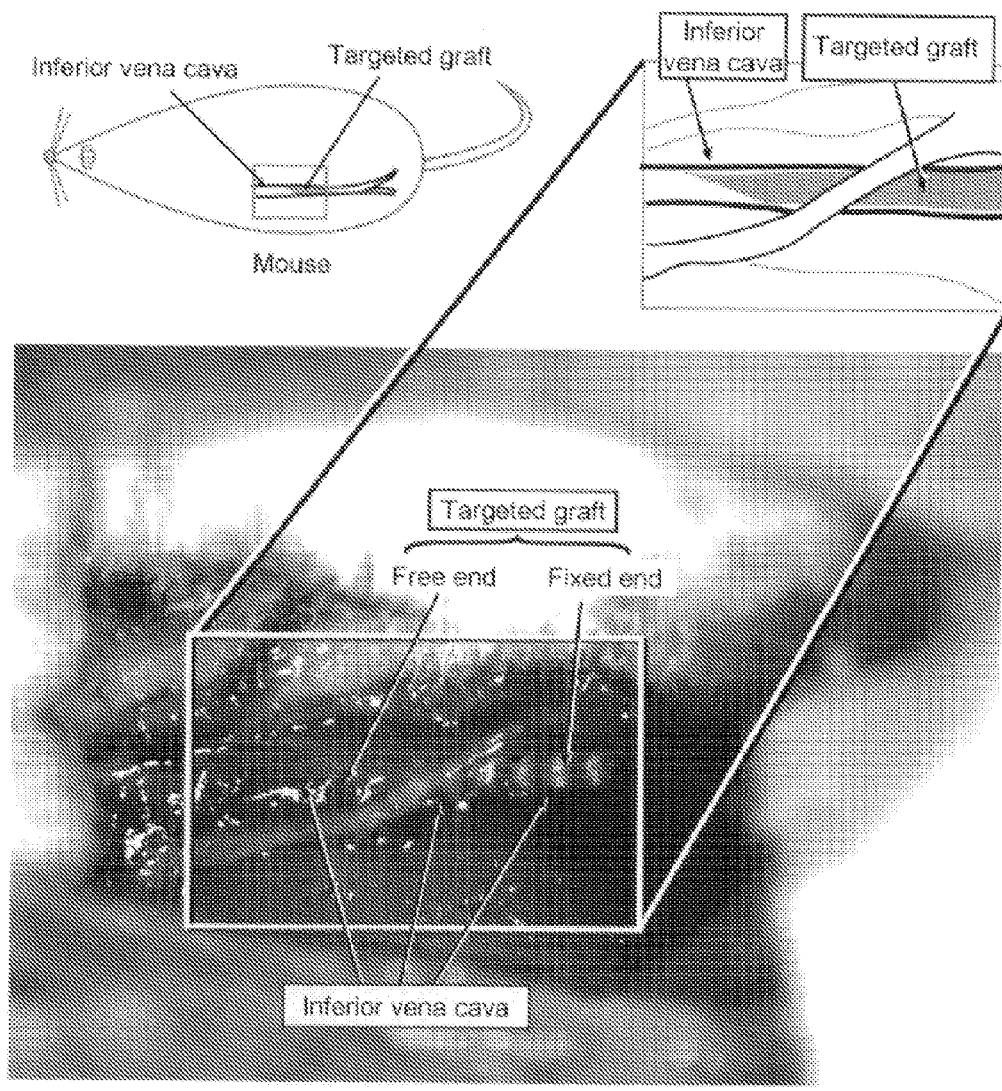
FIG. 7 shows a conceptual diagram of a targeted graft implanted inside the inferior vena cava of a mouse and a photograph of the same used as a substitute for diagram.

The targeted graft prepared beforehand by binding neutravidin to a biotinylated graft was implanted in the inferior vena cava of a mouse under general anesthesia. The targeted graft was inserted into the inferior vena cava (FIG. 7), the tail side (right side in the figure) of the graft was fixed to the blood vessel wall (fixed end), and the head side (left side in the figure) was allowed to float inside the blood vessel (free end).

Figure 8:
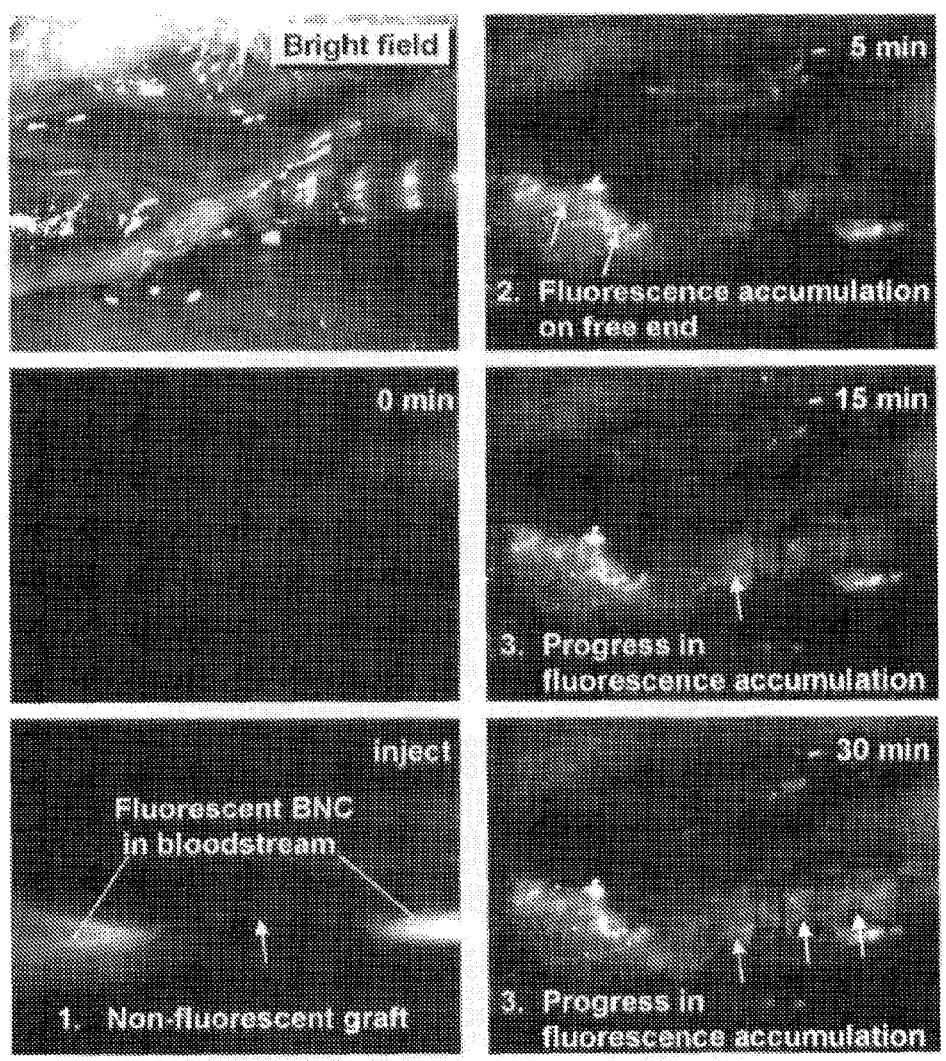
FIG. 8 shows photographs as a substitute for diagrams that indicate in vivo accumulation of target-recognizing nanocarriers on a targeted graft.
Figure 9:
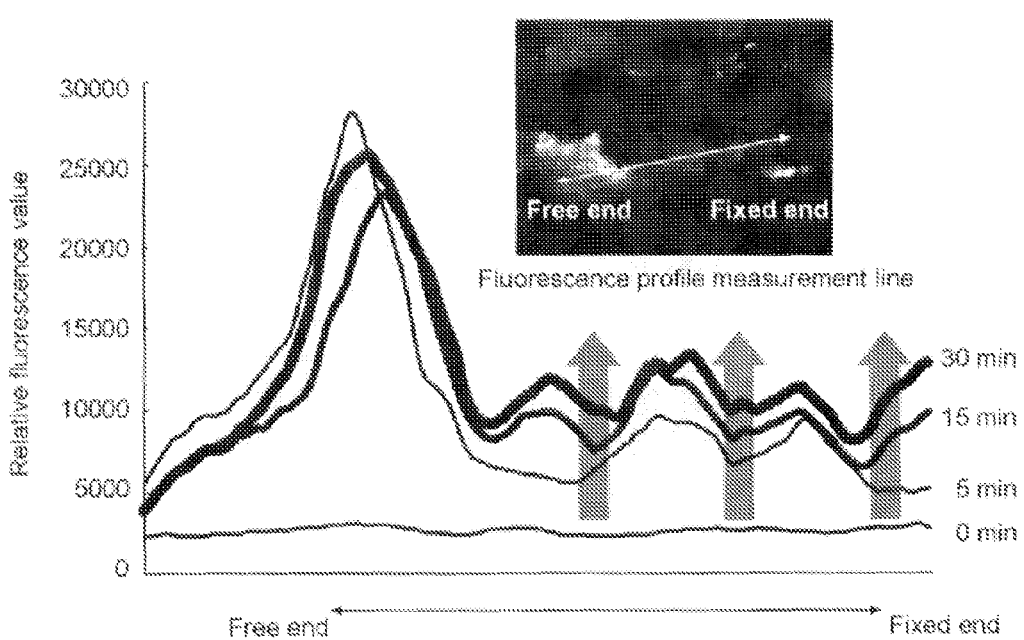
FIG. 9 is a graph showing in vivo accumulation of target-recognizing nanocarriers on the targeted graft.

After the targeted graft was implanted inside the blood vessel, Cy3-fluorescent labeled and biotinylated target-recognizing nanocarriers (biotinylated bio-nanocapsules=BNCs) (50 μg) were intravenously administered. Immediately after administration of fluorescent-labeled BNC ("inject" in FIG. 8), fluorescent signals of free BNCs were merely observed in the bloodstream and no fluorescence of BNCs was observed on the graft. However, 5 minutes later, fluorescence accumulation was observed on the free end side of the targeted graft. Thereafter, fluorescence accumulation was also confirmed on the fixed-end side over time ("15 min" and "30 min" in FIG. 8). In addition, FIG. 9 is a graph showing quantitative fluorescence profile determination results. The above results show that target-recognizing nanocarriers accumulate on a targeted graft in a blood vessel.

All publications, patents, and patent applications cited herein are incorporated herein by reference in their entirety.

INDUSTRIAL APPLICABILITY

It is expected that the drug delivery system of the present invention allows the use of the following drugs at appropriate local concentrations: drugs for which it has thus far been difficult to achieve effective local concentrations; and drugs which have been difficult to use due to adverse effects on tissues that are not sites of action. In addition, since drugs can be recharged in the system of the present invention, continuous drug delivery can be achieved by repeating drug recharge within the effective periods. Further, if a drug with better efficacy than a relevant conventional drug is developed, it is possible to administer target-recognizing nanocarriers in which such a drug to be delivered to a relevant lesion is newly encapsulated to deliver the drug to an indwelling medical device. This makes it possible to carry out more excellent treatment. Moreover, for an infectious disease in tissue surrounding an indwelling medical device, therapeutic drugs optimal for causative pathogens can be selected after infection, and a single or a plurality of therapeutic drugs can be simultaneously administered.

The invention claimed is:

1. A drug delivery system comprising an indwelling medical device having target molecules on its surface, said system further comprising target-recognizing bio-nanocapsules in which drugs are encapsulated,
    wherein said target-recognizing bio-nanocapsules have, on their surfaces, target-recognizing molecules capable of specifically binding to said target molecules,
    and wherein said bio-nanocapsules are nano-size capsules each comprising a lipid bilayer membrane and a virus surface antigen-derived particle.

2. The drug delivery system according to claim 1, wherein the indwelling medical device is coated with a biocompatible material and is targeted as a result of any of the following:
    1) surface modification of the biocompatible material to bind appropriate target molecules thereto;
    2) using the biocompatible material to which appropriate target molecules are pre-bound; and
    3) using the biocompatible material to which appropriate functional groups are pre-bound and then appropriate target molecules that are designed to react with the functional groups are bound.

3. The drug delivery system according to claim 1 or 2, wherein the target molecule carried by the indwelling medical device is selected from the group consisting of biotin, glutathione, a sugar, and an epitope.

4. The drug delivery system according to claim 1 or 2, wherein the target-recognizing molecules on the surfaces of said target-recognizing bio-nanocapsules are designed to bind to the target molecules on the surface of the indwelling medical device to, allow sustained-release of the encapsulated drugs from said target-recognizing bio-nanocapsules, or to allow introduction of the target-recognizing bio-nanocapsules into surrounding tissues with subsequent release of the encapsulated drugs from said target-recognizing bio-nanocapsules in said surrounding tissues.

5. The drug delivery system according to claim 1 or 2, wherein said system is for use in the treatment of an aneurysm, wherein the indwelling medical device is a stent graft, and wherein said target-recognizing bio-nanocapsules are target-recognizing bio-nanocapsules in which drugs having c Jun N-terminal kinase inhibitory activity are encapsulated.

6. The drug delivery system according to claim 1, wherein the bio-nanocapsules are nano-size capsules each comprising a lipid bilayer membrane and a hepatitis B virus surface antigen-derived particle.

7. The drug delivery system according to claim 3, wherein the biotin, glutathione, sugar, or epitope is modified with a spacer arm selected from the group consisting of a polyethylene glycol or a hydrocarbon;
    or wherein the biotin, glutathione, sugar, or epitope is modified with a reaction group selected from the group consisting of an N-hydroxysuccinimide group, a sulfo-N-hydroxysuccinimide group, a pentafluorophenyl group, a hydrazide group, an amide group, a pentylamine group, a maleimide group, a hexyl(pyridyldithio) propionamide group, an iodoacetyl group, a ridyl group, an azidosalicylamide group, a nitrophenyl azide group, a psoralen group, or a tetraphenylfluoroazido group.

* * * * *